(12) United States Patent
Makker et al.

(10) Patent No.: US 8,956,684 B2
(45) Date of Patent: *Feb. 17, 2015

(54) IOL INSERTION APPARATUS AND METHODS FOR MAKING AND USING SAME

(75) Inventors: Harish Makker, Mission Viejo, CA (US); Can Hu, Irvine, CA (US); Michael D. Lowery, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/622,554

(22) Filed: Nov. 20, 2009

(65) Prior Publication Data

US 2010/0129523 A1 May 27, 2010

Related U.S. Application Data

(60) Continuation of application No. 11/146,983, filed on Jun. 7, 2005, now Pat. No. 7,687,097, which is a division of application No. 10/608,875, filed on Jun. 27, 2003, now abandoned.

(51) Int. Cl.
| | |
|---|---|
| *B05D 3/02* | (2006.01) |
| *B05D 3/06* | (2006.01) |
| *C08J 7/18* | (2006.01) |
| *B29C 71/02* | (2006.01) |

(Continued)

(52) U.S. Cl.
CPC .............. *A61F 2/1664* (2013.01); *A61F 2/1675* (2013.01); *A61F 2/1678* (2013.01); *A61F 2/167* (2013.01)
USPC ........... 427/2.28; 427/2.1; 427/230; 427/236; 427/532; 427/541; 427/553; 606/107; 623/6.11; 623/6.12

(58) Field of Classification Search
USPC ........... 623/6, 6.11, 6.12; 427/2.1, 2.24, 2.28, 427/551, 557, 558, 532, 541, 553; 606/107
See application file for complete search history.

(56) References Cited

U.S. PATENT DOCUMENTS

| | | | |
|---|---|---|---|
| 5,263,992 A | 11/1993 | Guire | |
| 5,290,548 A | * 3/1994 | Goldberg et al. | .......... 424/78.18 |
| 5,429,839 A | 7/1995 | Graiver et al. | |

(Continued)

FOREIGN PATENT DOCUMENTS

WO      WO 9622062 A1  * 7/1996

OTHER PUBLICATIONS

Koleske, Joseph.Dual Cure Mechanisms, in Radiation Curing of Coatings, Chapter 9, pp. 155-164, ASTM International (2002).*

(Continued)

*Primary Examiner* — Cachet Sellman
(74) *Attorney, Agent, or Firm* — Abbott Medical Optics Inc.

(57) ABSTRACT

Apparatus, and methods of making and using apparatus, for inserting intraocular lenses (IOLs) are disclosed. The apparatus includes a hollow tube having an interior wall defining a hollow space through which an intraocular lens may be passed from the open space into an eye. A lubricity enhancing component is covalently bonded to the hollow tube at the interior wall in an amount effective to facilitate the passage of the intraocular lens through the hollow space. The lubricity enhancing component includes a substituent component effective to reduce hydrolysis of said lubricity enhancing component relative to an identical lubricity enhancing component without the substituent component.

10 Claims, 3 Drawing Sheets

(51) Int. Cl.
*A61F 9/00* (2006.01)
*A61F 2/16* (2006.01)

(56) References Cited

U.S. PATENT DOCUMENTS

| | | | |
|---|---|---|---|
| 5,525,691 | A | 6/1996 | Valint, Jr. et al. |
| 5,538,512 | A * | 7/1996 | Zenzon et al. ............... 604/508 |
| 5,803,925 | A * | 9/1998 | Yang et al. .................. 606/107 |
| 6,187,042 | B1 | 2/2001 | Sheets, Jr. et al. |
| 6,287,707 | B1 | 9/2001 | Luthra et al. |
| 6,348,242 | B1 * | 2/2002 | Daly et al. .................. 427/558 |
| 6,447,835 | B1 * | 9/2002 | Wang et al. ................. 427/2.24 |
| 6,632,905 | B2 * | 10/2003 | Leboeuf ..................... 526/303.1 |
| 6,645,246 | B1 * | 11/2003 | Weinschenk et al. ........ 623/6.37 |
| 2002/0133072 | A1 | 9/2002 | Wang et al. |
| 2003/0083433 | A1 * | 5/2003 | James et al. ................. 525/54.5 |

OTHER PUBLICATIONS

Broer D.J., et al., "Temperature Effects on the Kinetics of Photoinitiated Polymerization of Dimethacrylates," Polymer, 1991, vol. 32 (4), pp. 690-695.

Rueggeberg F.A., et al., "Effect of Photoinitiator Level on Properties of a Light-Cured and Post-Cure Heated Model Resin System," Dental Materials, 1997, vol. 13 (5-6), pp. 360-364.

* cited by examiner

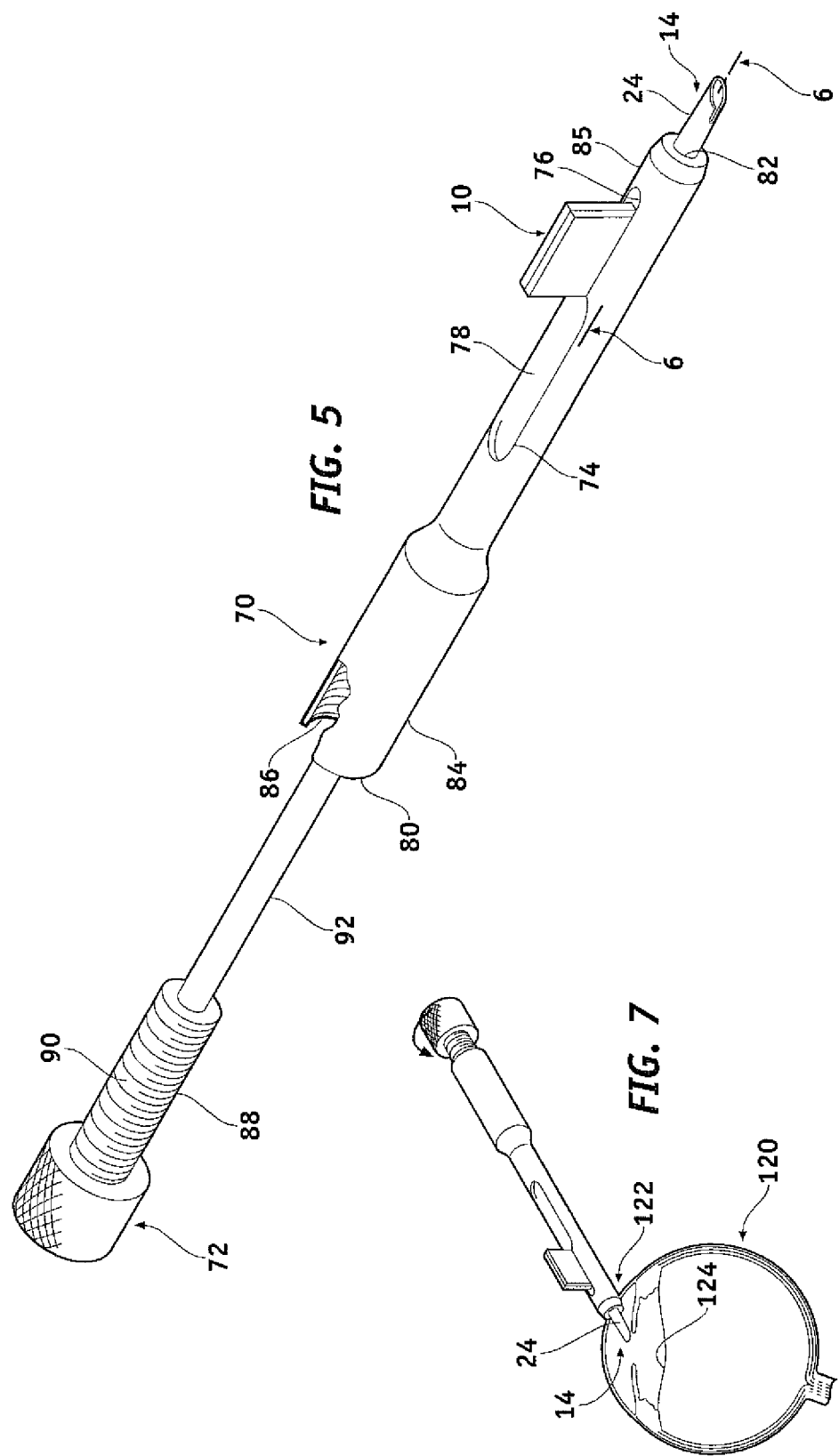

IOL INSERTION APPARATUS AND METHODS FOR MAKING AND USING SAME

This application claims priority to and is a continuation of U.S. application Ser. No. 11/146,983, filed Jun. 7, 2005, now U.S. Pat. No. 7,687,097, which is a divisional application of U.S. application Ser. No. 10/608,875, filed Jun. 27, 2003, now abandoned, each of which is hereby incorporated by reference in its entirety.

BACKGROUND OF THE INVENTION

The present invention relates to apparatus for inserting an intraocular lens through a small incision into an eye, to methods for making such apparatus and to methods for inserting an intraocular lens into an eye. More particularly, the present apparatus has enhanced lubricity and stability, can be relatively easily and effectively manufactured, and is useful for inserting a foldable intraocular lens into an eye.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one flexible fixation member or haptic which extends from the optic and becomes affixed in the eye to secure the lens in position. The optic normally includes an optically clear lens. Implantation of such IOLs into the eye involves making an incision in the eye. It is advantageous, to reduce trauma and speed healing, to have an incision size as small as possible.

IOLs are known which are foldable (deformable) so that the IOL can be inserted through a smaller incision into the eye. A substantial number of instruments have been proposed to aid in inserting such a foldable lens in the eye.

Many of the prior art IOL insertion systems load and/or fold the lens at the distal end, that is, at the end inserted into, or closest to, the eye. Such "distal loading" systems often disadvantageously include a space consuming loading component at or near the distal end of the system which causes the distal end to be relatively large. This relatively large distal end makes inserting the IOL through a small incision more difficult, if not impossible. Systems which fold and load the IOL proximally of the distal end provide certain advantages, such as reduced stress on the IOL and/or inserter, relative to "distal loading" systems.

However, whether using a distal loading or proximal loading system, one factor which has historically determined the minimum diameter of the inserter tube involves the inserter tube itself. For example, the material from which the inserter tube is made, such as polypropylene and the like polymeric materials, may have a relatively high coefficient of friction, causing it to provide a relatively high amount of resistance to an optic made, for instance, from silicone polymeric materials, as it passes through the tube. The amount of resistance, and thus the amount of force (torque) required to pass an IOL through the tube, increases as the diameter of the tube decreases. Since increased torque on the IOL increases the potential for damage to the IOL and/or the inserter tube, as well as injury to the patient, it is desirable to keep the required torque as low as possible.

One way to reduce the amount of force needed to pass an IOL through a small diameter insertion tube is to provide a lubricity enhancing component, such as a coating, on the exposed interior surfaces of the inserter. Examples of IOL inserters having an interior wall coated or otherwise provided with a lubricity enhancing component include Makker et al. U.S. Pat. No. 5,716,364 and Yang et al. U.S. Pat. No. 5,803,925. The disclosures of each of these patents are incorporated in their entireties herein by reference.

The aforementioned Makker patent discloses a method of making an inserter that comprises compounding a hydrophilic lubricity enhancing component such as glycerol monostearate (GMS) into the polypropylene resin used to fabricate the inserter. The interior wall is preferably then exposed to plasma and subsequently subjected to elevated temperatures for a sufficiently long time to cause the lubricity enhancing component to Abloom@ to the surface of the cartridge. After blooming, the lubricity enhancing component functions as a low-friction coating that is non-covalently bonded to the interior wall of the inserter.

The Yang et al. patent discloses an inserter having a lubricity enhancing component covalently bonded to an interior wall. An exemplary lubricity enhancing component disclosed in Yang et al. comprises a compound having the formula A-PEG, where A is a reactive group capable of covalently bonding to the surfaces of a polypropylene IOL inserter, and PEG is a residue of polyethylene glycol.

While many of the prior art lubricity enhancing components are generally satisfactory, further improvements are desirable. For instance, in inserters having non-covalently bonded GMS-based lubricity enhancing components such as those disclosed in the aforementioned Makker et al. patent, the blooming process may continue even after exposure of the inserter interior wall to high temperatures has stopped, which can eventually result in excessive amounts of GMS on the surface of interior wall. Such inserters have the potential of causing excess GMS to be transferred onto the surface of an IOL optic during insertion, causing unsightly blemishes or streaks on the optic. The shelf life of these prior art GMS-based cartridges is limited to one year, for example, to avoid this potential risk. On the other hand, prior art cartridges having covalently bonded lubricity enhancing components may involve more complex manufacturing processes, require higher torque to pass the IOL through the tube, or may be the potential risk of reduced stability, for example, because of hydrolysis of the coating, over time. Such prior art cartridges also have limited shelf life to avoid this potential stability risk. Likewise, a simplified mode of generating an appropriate matrix for cross-linking of involved subsistent for example a dialdehyde and a polymeric amine prior to dispersal and/or avoidance of extended times associated with plasma treatment serves to enhance industrial efficiency and is progress in science as a useful art.

Accordingly, it would be advantageous to provide stable, long-lasting lubricity-enhancing coatings for IOL insertion apparatus which facilitate the passage of folded IOLs through the apparatus in a controlled manner without using excessive force. It would also be advantageous to devise cost-effective and simple methods of making and using insertion apparatus.

SUMMARY OF THE INVENTION

New apparatus for injecting IOLs and methods for making and using such apparatus have been discovered. The present apparatus achieve enhanced lubricity, thus providing for controlled insertion of an IOL into an eye, for example, for the use of effective, reliable and non-excessive amounts of force to inject a folded IOL into an eye. The present system provides for controlled, reliable, easy and convenient insertion of IOLs, including those made of materials which would ordinarily exert relatively high frictional forces against the interior wall of the inserter. In addition, the present invention provides for inserting folded IOLs through very small incisions in the eye. The present IOL insertion methods are straightforward, easy to practice, and involve little or no modification of surgical techniques. The methods for making the insertion apparatus are also straightforward and easy to practice.

In general, the present invention involves apparatus for inserting IOLs into an eye which include an improved lubricity enhancing component covalently bonded to the apparatus, for example, at the interior hollow wall defining a hollow space through which an IOL is passed, to at least assist in facilitating the passage of the IOLs through the apparatus. Covalent attachment or bonding of such lubricity enhancing components is particularly effective since the amount of such component present and therefore, at least to some extent, the degree of enhanced lubricity, is conveniently controlled and stable on a long term basis, for example has a long term shelf life. In addition, there is reduced chance or risk of the lubricity enhancing component being disadvantageously removed from the surface of the apparatus as the IOL passes through the apparatus into the eye.

The use of the present covalently bonded lubricity enhancing components allows successful injection of foldable IOLs, such as silicone-based IOLs, foldable acrylic-based IOLS and the like, including those which would ordinarily exert relatively large frictional forces against the interior wall of the inserter, employing inserters made, for instance, of polypropylene and the like polymeric materials, through incisions about 3.5 mm or less, preferably about 3.0 mm or about 2.8 mm or less, and still more preferably less than 2.8 mm. Furthermore, relatively little force is required to perform the injection.

In one broad aspect of the invention, apparatus for inserting an intraocular lens through a small incision into an eye are provided. Such apparatus comprise a hollow tube including an interior wall defining a hollow space through which an intraocular lens may be passed from the hollow space into the eye. An improved lubricity enhancing component is covalently bonded to the hollow tube at the interior wall in an amount effective to facilitate the passage of the intraocular lens through the hollow space. The lubricity enhancing component includes a substituent component effective to increase the stability, for example, the chemical stability, preferably to reduce hydrolysis, of the lubricity enhancing component relative to an identical lubricity enhancing component without the substituent component.

In a particularly useful embodiment, the substituent component of the lubricity enhancing component is selected from non-hydroxy groups, that is, the substituent component is other than hydroxy, and is effective to reduce hydrolysis of the lubricity enhancing component relative to an identical lubricity enhancing component including one or more hydroxy groups in place of the substituent component.

In one embodiment of the invention, the substituent component is selected from the class consisting of hydrocarbyl groups, substituted hydrocarbyl groups and mixtures thereof. Preferably, the substituent component has 1 to about 4 carbon atoms per group. As used herein, the term hydrocarbyl groups means groups made up of carbon and hydrogen, such as alkyl, alkenyl and the like. Substituted hydrocarbyl groups are groups including carbon and hydrogen atoms and one or more other hetero atoms, such as one or more oxygen, nitrogen, phosphorous, sulfur and the like atoms, and mixtures thereof.

In an advantageous embodiment of the invention, the substituent component is selected from the class consisting of alkoxy groups having 1 to about 4 carbon atoms and mixtures thereof.

In a very useful embodiment, the substituent component is selected from one or more methoxy groups.

In yet another embodiment, the lubricity enhancing component is derived from a precursor component including the substituent component, an alkylene oxide component, for example in the form of a polyalkylene glycol component and the like, and an additional substituent component effective to covalently bond with at least one of the precursor component and the hollow tube. The precursor component includes at least one reactive substituent component effective to covalently bond to the hollow tube, for example, to the polymeric material of the hollow tube. In a particularly useful embodiment, the alkylene oxide component is an ethylene oxide component, for example a polyethylene glycol component. The additional substituent component advantageously is an ethylenically unsaturated group. Preferably, the additional substituent component is selected from the class consisting of vinyl groups, acrylic groups, methacrylic groups and mixtures thereof. In a more preferred embodiment, the precursor component is methoxy polyethylene glycol monomethacrylate (mPEGMA). Advantageously, the precursor component includes mPEGMA of two or more, preferably three, different molecular weights.

The hollow tube is preferably made of a polymeric material, more preferably selected from polypropylene and the like materials. In addition, the hollow tube is preferably sized to pass the intraocular lens into the eye through an incision no larger than 3.5 mm. More preferably, the tube is sized to pass the intraocular lens into the eye through an incision no larger than 3.0 mm. More preferably still, the tube is sized to pass the intraocular lens into the eye through an incision no larger than 2.8 mm.

The apparatus of the present invention also preferably includes a loading portion sized and adapted to receive an IOL for passage into the hollow space of the tube. The loading portion is preferably sized and adapted to receive the IOL in an unfolded state, and to hold the IOL in a folded state. The loading portion can be structured to at least facilitate the folding of the IOL from the unfolded state to a folded state. The hollow space of the tube is preferably sized to receive the IOL in a folded state from the loading portion and to pass the folded IOL to an open outlet through which the IOL is passed into an eye. Preferably, the lubricity enhancing component is provided on both the hollow tube and the loading portion of the apparatus.

Methods for inserting an IOL into an eye are included within the scope of the present invention. In one embodiment, such methods comprise placing an outlet of a hollow tube in or near an incision in an eye, and passing the intraocular lens from the hollow tube through the outlet into the eye. The hollow tube includes an interior wall defining a hollow space containing an IOL, preferably in a folded state. An improved lubricity enhancing component is provided and is covalently bonded to the hollow tube at or near the interior wall. The lubricity enhancing component includes a substituent component effective to enhance the stability, for example, the chemical stability, preferably to reduce hydrolysis of, the lubricity enhancing component relative to an identical lubricity enhancing component without the substituent component. Useful substituent components are disclosed elsewhere herein.

Methods of making an intraocular lens inserter apparatus are provided and included within the scope of the present invention. In one embodiment, such methods comprise contacting the interior wall of a hollow polymeric tube with a precursor material of an improved lubricity enhancing component and causing the precursor material to form the lubricity enhancing component covalently bonded to the polymeric material of the tube. The lubricity enhancing component includes at least one substituent group effective to increase the stability, for example the chemical stability, preferably to reduce hydrolysis, of the lubricity enhancing component relative to an identical lubricity enhancing component without the substituent component.

In one useful embodiment, the method includes a step of priming or pre-treating the interior wall, for instance by exposing the interior wall to plasma for a sufficient amount of time to enhance covalent bonding between the lubricity enhancing agent and the polymeric material of the tube, for example, so that the exposed surface of the wall is, or becomes, more susceptible to being wetted by the solution of the precursor material.

In an especially useful embodiment, the precursor material includes radical initiators, for instance UV and/or thermal radical initiators. The step of causing the precursor material to form a covalently bonded lubricity enhancing component preferably includes exposing the coating on the interior wall, for example the wetted interior wall, to conditions suitable for activating the initiator or initiators to form a covalently bonded coating on the interior surface of the tube. Advantageously, the precursor material includes both UV and thermal radical initiators, and the step of exposing the precursor material to conditions suitable for activating the initiators includes a first stage of exposing the coating on the wall to ultraviolet light to covalently bond the coating to the wall, and a second stage of exposing the covalently bonded coating to elevated temperatures for a time sufficient to enhance the stability of the covalently bonded coating.

Each and every feature described herein, and each and every combination of two or more of such features, is included within the scope of the present invention provided that the features included in such a combination are not mutually inconsistent.

These and other aspects of the present invention will become apparent in the following detailed description and claims, particularly when considered in conjunction with the accompanying drawings in which like parts bear like reference numerals.

BRIEF DESCRIPTION OF THE DRAWINGS

FIG. 5 is a front side view, in perspective, of the IOL inserter shown in FIG. 4 loaded into a hand piece.

FIG. 7 is a somewhat schematic illustration showing the IOL inserter shown in FIG. 5, with the hand piece partially in cross-section, being used to insert an IOL into an eye.

DETAILED DESCRIPTION OF THE DRAWINGS

Figure 1:
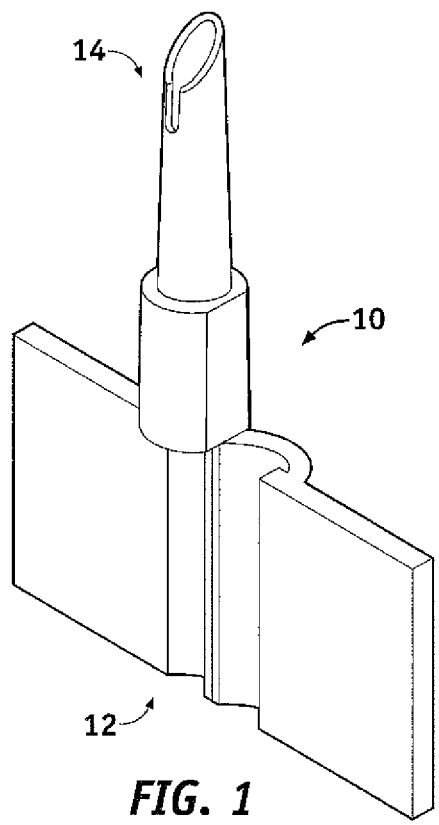
FIG. 1 is a schematic illustration showing an IOL inserter in accordance with the present invention including a covalently bonded lubricity enhancing component thereon.

FIG. 1 illustrates an IOL inserter, shown generally at 10, including a load chamber 12 and an injection tube 14. In FIG. 1, the IOL inserter 10, which is made of polypropylene, is shown after treatment with a lubricity enhancing precursor material. Preferably, the precursor material is selectively applied so that only the interior surfaces of the IOL inserter 10 are coated. This selective application may be achieved in any suitable manner such as by brushing with a microbrush, or by spraying, irrigating, or the like. Less desirably, the entire inserter 10 may be immersed in a bath of the precursor material so that both interior and exterior surfaces are coated.

Figure 2:
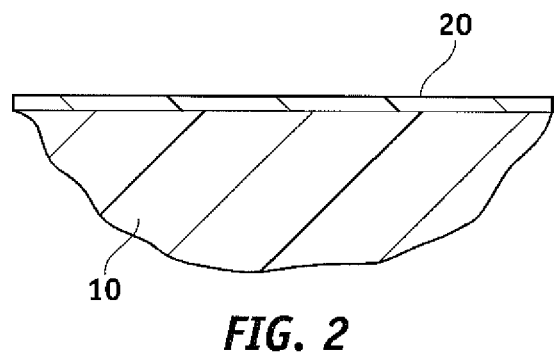
FIG. 2 is a fragmentary illustration of a small part of the IOL inserter shown in FIG. 1.
Figure 3:
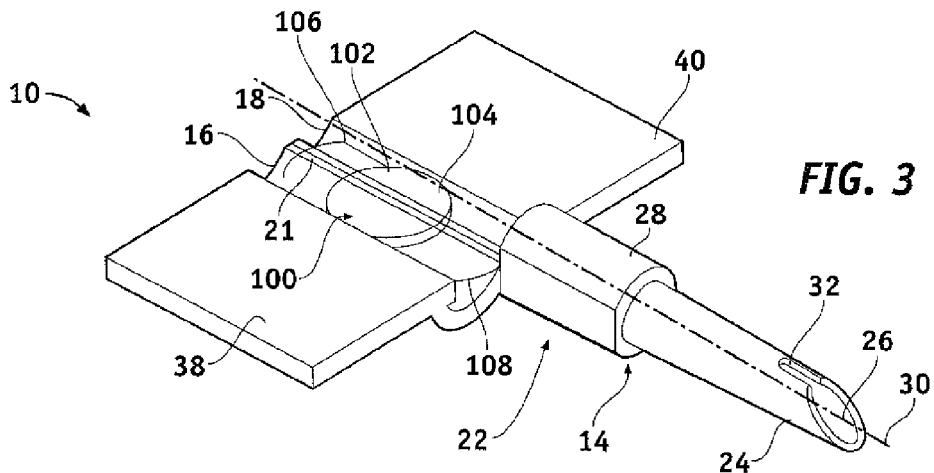
FIG. 3 is a front side view, in perspective, of an IOL inserter in accordance with the present invention, with the load chamber in the open position.

The purpose of treating IOL inserter 10 with the precursor material is to coat all of the tubular interior surfaces of IOL inserter 10 with a hydrophilic component, or coating, 20, as shown in FIG. 2. Coating 20 is covalently bonded to the inserter 10, that is, to the polypropylene. Coating 20, which enhances the lubricity of IOL inserter 10, for example of the lumens defined by load chamber 12 and injection tube 14, as shown in FIG. 3, relative to the lubricity of an identical IOL inserter without the covalently bonded coating 20. Such enhanced lubricity is effective to at least assist in facilitating the passage of an IOL through the lumens of IOL inserter 10 into an eye.

The precursor material of the lubricity enhancing component, preferably a hydrophilic material, contains reactive groups or substituents that allow at least limited covalent attachment to the polypropylene cartridge.

Importantly, the precursor material and the final coating 20 include substituent groups effective to enhance the stability, for example the storage stability or shelf life, of the IOL inserter 10 relative to an identical IOL inserter including a lubricity enhancing component without the substituent groups. Preferably, the substituent groups are effective to reduce hydrolysis of the lubricity enhancing coating relative to an identical lubricity enhancing coating or component without the substituent groups.

Advantageously, the substituent groups are not —OH groups, that is, are non-hydroxy groups. For instance, and without limitation, the substituent component may be selected from the class consisting of hydrocarbyl groups, substituted hydrocarbyl groups, and mixtures thereof, preferably such groups having 1 to about 4 carbon atoms per group. In a very useful embodiment, the substituent component is selected from alkoxy groups, preferably alkoxy groups having 1 to about 4 carbon atoms per group, and mixtures thereof. A particularly useful substituent component is one or more methoxy groups.

In one embodiment, the lubricity enhancing component or coating is derived from a hydrophilic, water soluble precursor component or material including the aforementioned substituent component or groups, an alkylene oxide component and the reactive substituent component or groups effective to covalently bond with the substrate, that is the polymeric material of the hollow tube. Such reactive groups, or at least a portion of such reactive groups, are effective to form homopolymers of the precursor material. The alkylene oxide component, for example, in the form of a polyalkylene glycol component and the like, may be selected from, for example, ethylene oxide components, propylene oxide components, and the like, and mixtures thereof. The alkylene oxide component is preferably an ethylene oxide component, for example a polyethylene glycol component. The reactive substituent component or groups are preferably selected from ethylenically unsaturated groups, and are more preferably selected from vinyl groups, acrylic groups, methacrylic groups, and the like, and mixtures thereof.

In an especially useful embodiment, the precursor material of the lubricity enhancing component is a hydrophilic, water soluble acrylic-based monomer such as methoxy polyethylene glycol monomethacrylate (mPEGMA). Coatings based on mPEGMA are very effective. In one advantageous embodiment, a coating utilizing a mixture of mPEGMA components of differing molecular weights, such as mPEGMA of three different molecular weights, has been found to be highly lubricious and stable. Without wishing to limit the invention to any particular theory of operation, it is believed that the heaviest, or highest molecular weight, mPEGMA component forms a relatively secure covalent bond with the polymeric material of the inserter tube, thus improving the stability of the coating, while the lightest, or lowest molecular weight, mPEGMA component is more loosely bound, providing enhanced lubricity.

One useful method of covalently bonding a lubricity enhancing component, such as mPEGMA or any of the other above-identified compositions, to IOL injection tube 14 is as follows. Non-compounded polypropylene resin is used to mold the tube 14 per normal manufacturing practice. Once the tube 14 is formed, it is exposed to an effective plasma for an effective amount of time to activate, or Aprime@, the exposed surfaces thereof so that such exposed surfaces are more susceptible to being wetted by a solution of the precursor material. The plasma may have its origin for any of a variety of materials, preferably gases, in particular gases such as oxygen, helium, nitrogen, argon, and the like and mixtures thereof. More preferably, a plasma containing a mixture of oxygen and argon is used.

In accordance with one embodiment of the present invention, the tube is subjected to plasma processing using a PS-150 plasma unit. The plasma includes oxygen at a flow rate of 20 cc/min and argon at a flow rate of 10 cc/min. The duration of treatment is about 5 minutes.

After plasma treatment, the precursor material is applied to the wall, for instance by spraying, brushing, immersion, irrigation, or the like. The precursor-coated, or wetted, wall is then exposed to conditions effective to cause the precursor material to form a lubricity enhancing component, or coating, having covalent bonds with the polymeric material of the tube. Then the coated wall is post-cured at conditions effective to enhance the stability of the coating.

Preferably, the precursor material includes radical initiators, for instance UV and/or thermal radical initiators. The step of causing the precursor material to form a covalently bonded lubricity enhancing component preferably includes exposing the coating on the interior wall to conditions suitable for activating the initiator or initiators. Advantageously, the precursor material includes both UV and thermal radical initiators, and the step of exposing the coating on the interior wall to conditions suitable for activating the initiator or initiators includes a first stage of exposing the coating on the wall to ultraviolet light to form a covalently bonded coating on the interior wall, and a second stage of exposing the covalently bonded coating on the wall to elevated temperatures for a time sufficient to enhance the stability of the covalently bonded coating. Preferably, after the coating has been exposed to the UV light and/or elevated temperatures, unreacted monomer is removed from the cartridge surface, for instance by washing.

Any suitable UV initiator and/or thermal initiator may be employed provided such materials have no substantial detrimental effect on the inserter, on the IOL to be inserted or on the patient in whose eye the IOL is inserted. Useful such initiators are well known and commercially available. In one useful embodiment, the UV initiator in the precursor material comprises a mixture of Bis(2,6-dimethoxybenzoyl)-2,4,4-trimethyl-pentylphosphineoxide, and 1-hydroxy-cyclohexyl-phenyl-ketone. This initiator is activated by exposing the precursor material to UV light for about 10 minutes. A useful thermal initiator in the precursor material comprises 2,5-dimethyl-2,5-bis(2-ethyl hexanoyl peroxy)hexane, which is activated by placing the inserter in an oven for an hour or more at 90° C. However, the specific initiators, exposure times, temperatures and/or other parameters may be varied depending on factors such as the equipment and the particular inserter and inserter components involved, and can readily be optimized based on the disclosure herein using routine experimentation.

A method of using the IOL inserter 10 according to the present invention is illustrated in FIGS. 3 to 7. The structure of the inserter 10, however, is merely illustrative of the inserters included within the scope of the present invention, and is not intended to be limiting. Inserters including the covalently bonded lubricity enhancing components described herein and having configurations substantially different from IOL inserter 10 are also included within the scope of the present invention.

The body of IOL inserter 10 (that is other than coating 20) is an integrally formed, for example, molded, unit made of non-compounded polypropylene. Load chamber 12 includes a first member 16 and a second member 18, hingedly secured to one another and moveable with respect to each other along line 21, which is parallel to the longitudinal axis 30 of the inserter 10.

Injection tube 14 includes a proximal end portion 22, a distal end portion 24 and an open distal end 26. A reinforcing collar 28 is coincidental with the proximal end portion 22 of injection tube 14. Injection tube 14 also includes a through slot 32.

As shown in FIG. 3, inserter 10 is in the opened position. In contrast, in FIG. 4, inserter 10 is shown in the closed position. In the closed position, the load chamber 12 includes a top 32 which is a combination of top surfaces 34 and 36 of first wing 38 and second wing 40, respectively. First and second wings 38 and 40 are effective for a human user of inserter to hold and manipulate the inserter 10 while using it, as described hereinafter.

Figure 4:
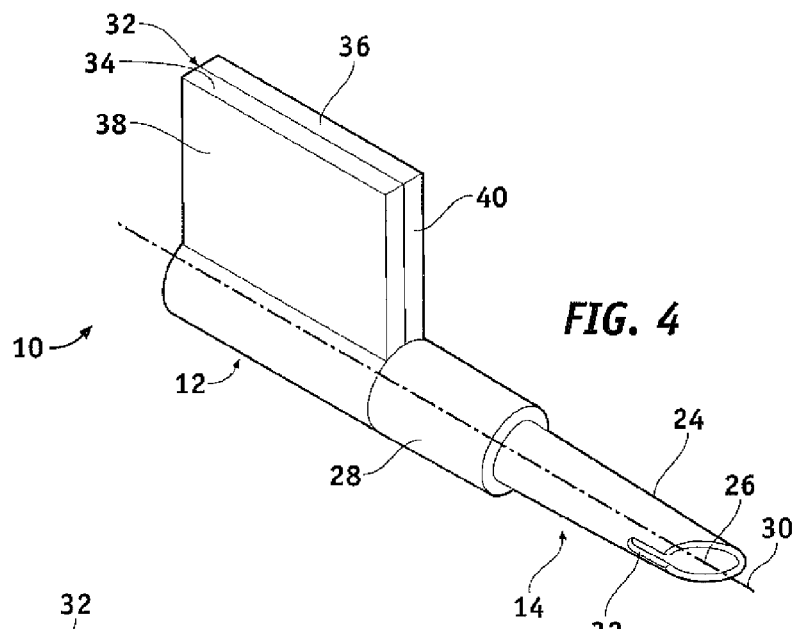
FIG. 4 is a side view, in perspective, of an IOL inserter in accordance with the present invention, with the load chamber in the closed position.

Inserter 10 is described in more detail with reference to FIG. 5, which shows the inserter in combination with hand piece 70. When used in combination with hand piece 70, the load chamber 12 of inserter 10 is in the closed position, as shown in FIG. 4.

Figure 6:
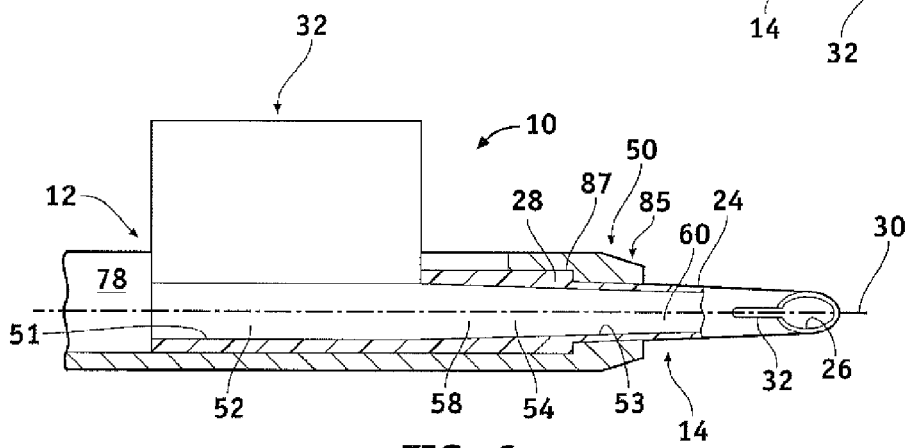
FIG. 6 is a side view, partly in cross-section, taken generally along line 6-6 of FIG. 5.

Referring to FIG. 6, with load chamber 12 in the closed position, the load chamber includes an interior wall 51 which defines a first lumen that is elongated in a direction parallel to the longitudinal axis 30 of inserter 10. Injection tube 14 includes a tapering interior wall 53 which defines a distally tapering second lumen 54.

The first lumen 52 is aligned with the second lumen 54 so that a folded IOL in the first lumen can be passed directly from the first lumen into the second lumen. The taper of proximal portion 58 of second lumen 54 is more severe than the slight taper which exists in the distal portion 60 of the second lumen. The more severe taper in the proximal portion 58 is effective to further fold the IOL as the IOL is passed into the second lumen. This further folding is advantageous because the further folded IOL can be inserted into the eye through a smaller incision. The coating 20 also advantageously reduces the risk of tearing and/or otherwise damaging the IOL as the IOL is passed through the first lumen 52 and the second lumen 54.

With reference to FIG. 5, inserter 10 is shown in combination with hand piece 70 and push rod member 72. Hand piece 70 includes a relatively large, elongated first through opening 74 and a relatively small, elongated second through opening 76. Hand piece 70 also includes a through bore 78 which extends from the proximal end 80 to the distal end 82 of the hand piece. The proximal end portion of hand piece 70 includes threads 86 adapted to engage and mate with threads 88 of the proximal segment 90 of push rod member 72. Rod element 92 of push rod member 72 is adapted to pass through bore 78, first lumen 52, second lumen 54 and out of open distal end 26. Hand piece 70 and push rod member 72 are made of metal, such as surgical grade stainless steel or the like metals. The distal end portion of rod member 72 can be made of a soft polymeric material, for example, configured to be introduced into and held in a fold of a folded IOL as the IOL is passed through the inserter.

Inserter 10 is operated and functions as follows. When it is desired to load an IOL into inserter 10, the inserter is placed, for example, manually placed, in a configuration as shown in FIG. 3. With load chamber 12 in the opened position, a quantity of an ophthalmically acceptable liquid is placed in the troughs formed by the first and second members 16 and 18 throughout the injection tube. This liquid component is effective, together with the lubricity enhancing component 20, in facilitating the passage of the IOL through the inserter 10. Although any suitable liquid component may be employed, particular useful are liquid aqueous components. Examples include liquid aqueous salt solutions, such as commercially available balanced salt solutions; and liquid aqueous media including visco elastic components, such as hyaluronate alkali metal salts, hydroxypropylmethyl cellulose, other water soluble cellulose derivatives, condroitin sulfate, mixtures thereof, and the like.

After the liquid component has been provided, an IOL, such as shown generally at 100, is placed, for example, using forceps, in between first and second members 16 and 18. This placement is such that the anterior face 102 of optic 104 faces upwardly, as shown in FIG. 3. The optic 104 is made of a silicone polymeric material. The filament haptics 106 and 108 of IOL 100 are located as shown in FIG. 3, so that the fixation members are located generally parallel to, rather than transverse to, the longitudinal axis 30.

With IOL 100 placed as shown in FIG. 3, first and second members 16 and 18 are hingedly moved relative to each other, for example, by manually bringing first and second wings 38 and 40 together, to place the load chamber 12 in the closed position, as shown in FIG. 4. With load chamber 12 in the closed position, IOL 100 is in a folded state, that is, optic 104 is folded. The relative movement of first and second members 16 and 18 to move the load chamber from the open position to the closed position is effective to fold the lens. The folded IOL 100 is now located in the first lumen 52. For clarity=s sake, the folded IOL is not shown in any of FIG. 4, 5, 6 or 7.

With the inserter 10 configured as shown in FIG. 4 and folded IOL 100 located in the first lumen 52, the inserter 10 is placed in association with hand piece 70, as shown in FIG. 5. In this configuration, the distal end portion 24 of injection tube 14 extends distally beyond the distal end 82 of hand piece 70. As shown in FIG. 6, the distal portion 85 of hand piece 70 includes an inner wall 87 which is configured to receive reinforcing collar 28 in abutting relation.

With inserter 10 so placed relative to hand piece 70, push rod member 72 is pushed in to the through bore 78 and into the inserter 10 to push the IOL 100 from the first lumen 52 into the second lumen 54. As the threads 88 come into contact with and engage threads 86, the push rod member 72 is rotated, as shown in FIG. 7, so as to thread the push rod member onto the proximal end portion 84 of hand piece 70. By gradually moving the push rod element 92 through bore 78 of hand piece 70, the folded IOL 100 is urged to move from first lumen 52 into second lumen 54, through the open distal end 26 and into the eye.

Referring now to FIG. 7, the IOL 100 is to be placed in eye 120 into an area formerly occupied by the natural lens of the eye. FIG. 7 shows the sclera 122 having an incision through which the distal end portion 24 of injection tube 14 is passed. Alternately, the incision can be made through the cornea. Distal end portion 24 has a sufficiently small cross-section to pass into the eye 120 through an incision in the sclera 122. Preferably the distal end portion is small enough in cross-section to pass through an incision as small as 2.8 mm or less.

The injection tube 14 is manipulated within eye 122 until it is positioned so that IOL can be properly positioned in eye, that is, in the anterior chamber, posterior chamber, capsular bag 124, or sulcus, after being released. Thus, the surgeon is able to controllably position the distal end portion 24 of injection tube 14, with IOL 100 in the first lumen 52 of load chamber 12. Once distal end portion 24 is so positioned, the rod element 92 is urged distally, by rotating (threading) push rod member 72 onto hand piece 70, to pass the IOL 100 into and through the second lumen 54, through the open distal end 26 of injection tube 14 and into the eye 120. The anterior face 102 of IOL 100 faces generally forwardly in the eye 120 as the IOL is released from the inserter 10. In other words, the IOL 100 passes through the first lumen 52, second lumen 54 and open distal end 26 and into eye 120 without flipping or otherwise becoming misplaced. Only a relatively small amount of, if any, post-insertion re-positioning is needed to properly position IOL 100 in the eye 120.

After the IOL 100 has been inserted into the eye, the rod element 92 is moved proximally into the injection tube 14 and the distal end portion of the injection tube is removed from the eye. If needed, the IOL 100 can be repositioned in the eye by a small, bent needle or similar tool inserted in the same incision.

Once the IOL 100 is properly positioned in eye 120 and inserter 10 is withdrawn from the eye, the incision in the sclera may be mended, for example, using conventional techniques. After use, inserter 10 is preferably disposed of. Hand piece 70 and push rod member 72 can be reused, after sterilization/disinfection.

The following non-limiting example illustrates certain aspects of the present invention.

Example

A precursor material is formed by mixing the following monomers in a suitable container.

| INGREDIENT | % BY WEIGHT |
| --- | --- |
| mPEGMA mw 1100 | 6.4% |
| mPEGMA mw 526 | 9.5% |
| mPEGMA mw 360 | 2.4% |
| thermal initiator (2,5-dimethyl-2,5-bis(2-ethyl hexanoyl peroxy)hexane) | 0.5% |
| photoinitiator (mixture of Bis(2,6-dimethoxybenzoyl)-2,4,4-trimethyl-pentylphosphineoxide and 1-hydroxy-cyclohexyl-phenyl-ketone) | 1.2% |
| Acetone | 80% |

The mixture is applied, using a microbrush, to the interior wall of a non-compounded polypropylene inserter cartridge which has been pretreated for 5 minutes with a plasma including 20 cc/min oxygen and 10 cc/min argon, using a PS-150 plasma unit. The wetted interior wall is then exposed to UV light for 10 minutes and post-cured in an oven for one hour or more at 90° C. After post-curing, any unreacted monomer is removed, for instance by washing the cartridge.

A series of tests is run to evaluate the lubricity of the above mPEGma-coated inserter cartridge (Cartridge A) in comparison to a control cartridge of the type sold by Advanced Medical Optics, Inc. (Santa Ana, Calif.) under the trademark Unfolder Sapphire Series Implantation System (Cartridge B), and to cartridges, identified below as Cartridges C, D, and E, coated with hydroxypropylmethyl cellulose (HPMC), poly 1-vinyl-2-pyrrolidinone (PVP), and polyethyleneglycol acrylate (PEGA), respectively. All the cartridges are identical to one another in structure and are semi-opaque.

The control cartridge, of the type described in the aforementioned Makker U.S. Pat. No. 5,716,364, is molded from polypropylene including 0.25% by weight of glycerol monostearate (GMS), and subjected to plasma processing and blooming processing, causing the GMS to be concentrated at or near, but not covalently bonded to, an interior wall of the cartridge.

Cartridges C, D, and E are formed from the same non-compounded polypropylene resin as cartridge A, and are subjected to the same pre-treating, curing and post-curing procedures as Cartridge A so that the coatings are covalently bonded to the cartridges.

A series of tests were run to evaluate the lubricity of various IOL inserters. The lenses used in the testing included optics made of acrylic based polymeric material. Specifically, the IOLs were those sold by Advanced Medical Optics, Inc. under the trademark Sensar® AR40e, brand of IOL (Santa Ana, Calif.).

The test procedure used is as follows. The IOL is loaded into the loading chamber and the inserter is placed into the hand piece. An amount of commercially available aqueous solution approximately equal to the volume of the IOL optic is dispensed into the loading chamber. In certain tests, the IOL is immediately advanced through the loading chamber and forward tube and then out the distal port. In other tests, the IOL is allowed to dwell in the loading chamber (Stage 1) for three minutes, advanced into the forward tube and then immediately released. In still other tests, the IOL is immediately advanced through the loading chamber, and then allowed to dwell in the forward tube (Stage 2) for three minutes before being released out the distal port.

The amount of torque required to advance the IOL through the inserter cartridge under the various dwell time scenarios is measured, and the results averaged for each inserter. The results are as follows:

| INSERTER | AVERAGE TORQUE (gm-cm) |
|---|---|
| A | 327 |
| B | 733 |
| C | 1117 |
| D | 792 |
| E | 871 |

These results indicate that Inserter A, which includes a covalently bonded mPEGMA coating in accordance with the present invention, requires lower torque to advance an IOL through the cartridge than is required by each of the other inserters, including the control inserter B, which includes a non-covalently bonded GMS lubricity enhancing component concentrated near its interior wall. Thus, a covalently bonded mPEGMA coating according to the present invention is demonstrated to be more lubricious than the prior art non-covalently bonded GMS lubricity enhancing component.

In addition, the present coatings, for example derived from mPEGMA of different molecular weights are more stable, e.g. allow the inserter to have a longer effective shelf life, relative to other coated inserters, whether the lubricity enhancing component is covalently bonded or not. The use of methoxy polyethylene glycol monomethacrylate (mPEGMA) is effective to reduce hydrolysis of the resulting coating relative to other coatings, such as polyethylene glycol monomethacrylate with no methoxy groups, and provides for a more stable coating.

While this invention has been described with respect to various specific examples and embodiments, it is to be understood that the invention is not limited thereto and that it can be variously practiced within the scope of the following claims.

What is claimed is:

1. A method of making an intraocular lens inserter cartridge, comprising:
   providing a semi-opaque cartridge comprising a polymeric material, wherein the cartridge comprises a hollow tube including an interior wall defining a hollow space through which an intraocular lens may be passed and an outlet through which the intraocular lens may be passed from the hollow space into an eye, wherein the outlet is configured to pass through an incision of 2.8 mm or less;
   contacting the interior wall of the tube with a precursor material of a lubricity enhancing component;
   exposing the precursor material of the lubricity enhancing component to ultraviolet (UV) light to form a covalently bonded coating on the interior wall of the tube; and
   exposing the covalently bonded coating on the interior wall of the tube to thermal radiation to enhance stability of the covalently bonded coating,
   wherein:
   the precursor material includes a thermal initiator and a UV initiator.

2. The method of claim 1, further comprising a step of exposing the interior wall to plasma for a sufficient amount of time to enhance the covalent bonding between the lubricity enhancing component and the polymeric material of the tube.

3. The method of claim 1, wherein the polymeric material comprises polypropylene.

4. The method of claim 1, wherein the lubricity enhancing component includes at least one substituent group effective to reduce hydrolysis of the lubricity enhancing component relative to an identical lubricity enhancing component without the at least one substituent group.

5. The method of claim 4, wherein the at least one substituent group is other than a hydroxy group.

6. The method of claim 5, wherein the at least one substituent group is selected from the group consisting of hyrdocarbyl groups, substituted hydrocarbyl groups and mixtures thereof.

7. The method of claim 4, wherein the at least one substituent group is selected from the group consisting of alkoxy groups having 1 to about 4 carbon atoms and mixtures thereof.

8. The method of claim 4, wherein the at least one substituent group is one or more methoxy groups.

9. The method of claim 4, wherein the at least one substituent group is effective to reduce hydrolysis of said lubricity enhancing component relative to an identical lubricity enhancing component including one or more hydroxy groups in place of the at least one substituent group.

10. The method of claim 1, wherein said precursor material of the lubricity enhancing component is hydrophilic.

* * * * *